(12) United States Patent
Osman

(10) Patent No.: US 8,663,326 B2
(45) Date of Patent: Mar. 4, 2014

(54) BIOLOGIC ARTIFICIAL BONE

(76) Inventor: Said G. Osman, Russellville, AL (US)

( * ) Notice: Subject to any disclaimer, the term of this patent is extended or adjusted under 35 U.S.C. 154(b) by 1179 days.

(21) Appl. No.: 11/955,684

(22) Filed: Dec. 13, 2007

(65) Prior Publication Data

US 2009/0157181 A1    Jun. 18, 2009

(51) Int. Cl.
*A61F 2/28* (2006.01)
*A61B 17/08* (2006.01)

(52) U.S. Cl.
USPC ........................................ 623/16.11; 606/151

(58) Field of Classification Search
USPC ............ 623/23.5, 23.51, 23.56, 23.57, 23.61, 623/23.62; 606/151
See application file for complete search history.

(56) References Cited

U.S. PATENT DOCUMENTS

| | | | |
|---|---|---|---|
| 3,769,142 A * | 10/1973 | Holmes et al. | 428/113 |
| 4,314,380 A | 2/1982 | Miyata et al. | |
| 5,141,510 A | 8/1992 | Takagi et al. | |
| 5,152,791 A | 10/1992 | Hakamatsuka et al. | |
| 5,314,478 A | 5/1994 | Oka et al. | |
| 5,639,402 A | 6/1997 | Barlow et al. | |
| 5,769,864 A * | 6/1998 | Kugel | 606/151 |
| 5,899,939 A * | 5/1999 | Boyce et al. | 623/16.11 |
| 6,149,688 A | 11/2000 | Brosnahan et al. | |
| 6,162,234 A * | 12/2000 | Freedland et al. | 606/151 |
| 6,183,515 B1 | 2/2001 | Barlow et al. | |
| 6,432,142 B1 | 8/2002 | Kamiya et al. | |
| 6,537,589 B1 | 3/2003 | Chae et al. | |
| 6,540,784 B2 | 4/2003 | Barlow et al. | |
| 6,607,557 B1 | 8/2003 | Brosnahan et al. | |
| 6,932,610 B2 | 8/2005 | Ono et al. | |
| 2004/0127987 A1* | 7/2004 | Evans et al. | 623/11.11 |
| 2004/0167637 A1* | 8/2004 | Biscup | 623/23.75 |

\* cited by examiner

*Primary Examiner* — David Isabella
*Assistant Examiner* — Yashita Sharma
(74) *Attorney, Agent, or Firm* — Nixon & Vanderhye P.C.

(57) ABSTRACT

A biologic artificial bone includes an artificial fiber material formed from a synthetic polymer with mechanical properties similar to type I collagen. A biocompatible liquid substance is impregnated in the fiber material that hardens and stiffens the fiber material. A bone substitute is impregnated in the hardened and stiffened fiber material forming an artificial bone composite. Vascular channels are formed in the artificial bone composite to facilitate in-growth of vessels and bone forming cells. The construction and methods achieve an artificial composite structure that is similar to natural bone with comparable properties.

18 Claims, 12 Drawing Sheets

BIOLOGIC ARTIFICIAL BONE

CROSS-REFERENCES TO RELATED APPLICATIONS (NOT APPLICABLE)

STATEMENT REGARDING FEDERALLY SPONSORED RESEARCH OR DEVELOPMENT (NOT APPLICABLE)

BACKGROUND OF THE INVENTION

The present invention relates to artificial bone and, more particularly, to biologic artificial bone having mechanical and biologic properties such that the artificial bone serves as an adequate substitute for structural bone.

The current standard for surgical treatment of fractures utilizes metal alloys for various techniques of fixation: plate and screws, wires, intra-medullary rods, pins, and artificial joint replacement. These devices are not absorbable and stay permanently in the bone and can be a problem in the future, requiring removal or replacements. Such complications may include, without limitation, implant loosening, prominence, discomfort, fracture, allergies, interference with CT and MRI scans, and the like.

Currently, the devices used to fill in bone defects include autografts, allografts, xenografts, metal implants. Each has its unique problems, ranging from donor site complications to substitute rejections and infections. More recently, ceramics have been used to fill in the bone defects, but these are not structural bone and are usually used as a supplement to a fixation procedure. Similarly bone morphogenic proteins are used as oste-inductive and osteogenic factors to encourage bone formation within the bone defects.

Various ceramics are currently in use in orthopedics and are mostly used as bone graft expanders. There is no structural artificial long bone, or cancellous bone such as a vertebral body currently available to replace or supplement host bones in conditions such as traumatic bone defect or surgical excision for tumor and infections. Allograft bone is currently used to replace large defects such as the different areas of femur.

BRIEF SUMMARY OF THE INVENTION

It would thus be desirable to develop a biologic artificial bone that is suitable to replace or supplemental host bones.

To adequately substitute for structural bone, the artificial bone preferably should include properties comparable to the host bone. Mechanical properties include tensile strength (polylactide glycolic acid, polyurethane urea, polycarbonate and similar materials), shear strength (polylactide glycolic acid, polyurethane urea, polycarbonate and similar materials), compressive strength (ceramics, berkeley university layered ceramic to mimic nacre), and bending strength (polylactide glycolic acid, polyurethane urea, polycarbonate). Biologic properties include biocompatibility, biodegradability, bio-incorporability, osteoconductive, osteo-inductive, osteo-genic, potential for hematopoiesis, and neo-vascularization.

Unfortunately, no single material has properties similar to the host bone, which is a composite of collagen, mineral, vessels, nerves and bone forming and bone resorbing cells, and blood forming cells. It is, therefore, desirable to produce a composite structure, similar to natural bone with comparable properties.

In an exemplary embodiment, a biologic artificial bone includes an artificial fiber material formed from a synthetic polymer with mechanical properties similar to type I collagen, and a biocompatible liquid substance impregnated in the fiber material. The biocompatible liquid substance serves to harden and stiffen the fiber material. A bone substitute is impregnated in the hardened and stiffened fiber material to form an artificial bone composite. Vascular channels are formed in the artificial bone composite to facilitate in-growth of vessels and bone forming cells. In a preferred arrangement, the artificial fiber material is formed into a cast shaped corresponding to a human bone. In a similar context, the artificial fiber material may be formed into a cast shaped corresponding to a bone implant.

In one embodiment, the artificial fiber material includes fibers formed in a fiber network with fibers arranged in horizontal, vertical and oblique orientations. In an alternative embodiment, the artificial fiber material includes fibers formed in a fiber network with fibers arranged in vertical, horizontal and spiral orientations defining a concentric cylindrical arrangement of fibers. In still another alternative, the artificial fiber material includes fibers formed in a fiber network with fibers arranged in vertical, horizontal and spiral orientations defining a fibrous sheet rolled into a multilayer cylinder.

Preferably, the bone substitute comprises ceramics. In addition, the channels may be coated with angiogenic factors. The artificial bone composite may be wrapped with a porous sheet of absorbable material having spikes of variable density on one side thereof, the porous sheet being wrapped on the artificial bone composite with the spikes facing inward to penetrate the artificial bone composite.

In another exemplary embodiment, a method of constructing a biologic artificial bone includes the steps of (a) forming an artificial fiber material from a synthetic polymer with mechanical properties similar to type I collagen; (b) impregnating the artificial fiber material with a biocompatible liquid substance, the biocompatible liquid substance hardening and stiffening the fiber material; (c) impregnating the hardened and stiffened fiber material with a bone substitute, thereby forming an artificial bone composite; and (d) forming vascular channels in the artificial bone composite to facilitate in-growth of vessels and bone forming cells.

Step (b) may be practiced while maintaining a predefined shaped of the artificial fiber material. Step (c) may be practiced by impregnating with ceramics. In this context, step (c) may be practiced by immersing the hardened and stiffened fiber material into a mold containing a liquid ceramic. Alternatively, step (c) may be practiced by placing the hardened and stiffened fiber material in a mold and pouring ceramic into the mold and allowing the ceramic to set. In still another alternative, step (c) may be practiced by grit-blasting the hardened and stiffened fiber material with ceramic.

In one embodiment, step (a) includes rolling the fiber material into a cylinder to produce a desired shape prior to step (b). The method may additionally include, prior to step (b), wrapping the fiber material with a porous sheet of absorbable material having spikes thereon facing the fiber material, wherein the spikes penetrate the fiber material. In this context, the method may additionally include, after step (c), removing the porous sheet of absorbable material by one of chemical dissolution, heating, and in vivo dissolution in body fluid.

The method may also include, prior to step (b), placing the fiber material in a mold including spikes facing the fiber material, the spikes on the mold penetrating the fiber material, and after step (c), removing the spikes.

Step (d) may be practiced by micro-drilling the channels.

BRIEF DESCRIPTION OF THE DRAWINGS

These and other aspects and advantages will be described in detail with reference to the accompanying drawings, in which.

DETAILED DESCRIPTION OF THE INVENTION

The embodiments described herein utilize a composite structure having a resulting arrangement with comparable properties to natural bone.

A base material is constructed of an artificial fiber to replace the collagens in bone. This fiber could be made from various synthetic polymers whose mechanical properties are similar to or stronger than type I collagen. The polymer matrix framework could be made into a cast in the shape of various bones, or the implants currently used to fix fractures as enumerated above.

Figure 1:
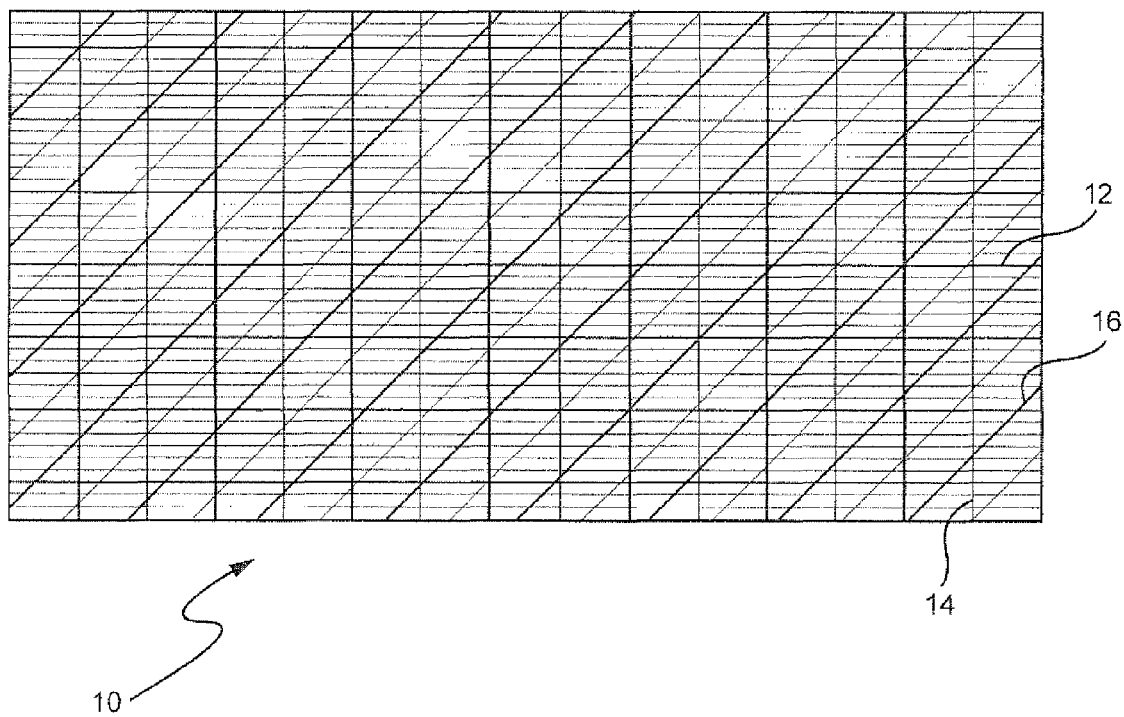
FIG. 1 shows an exemplary polymer matrix/network of fibers used to develop a framework of the device.
Figure 2A:
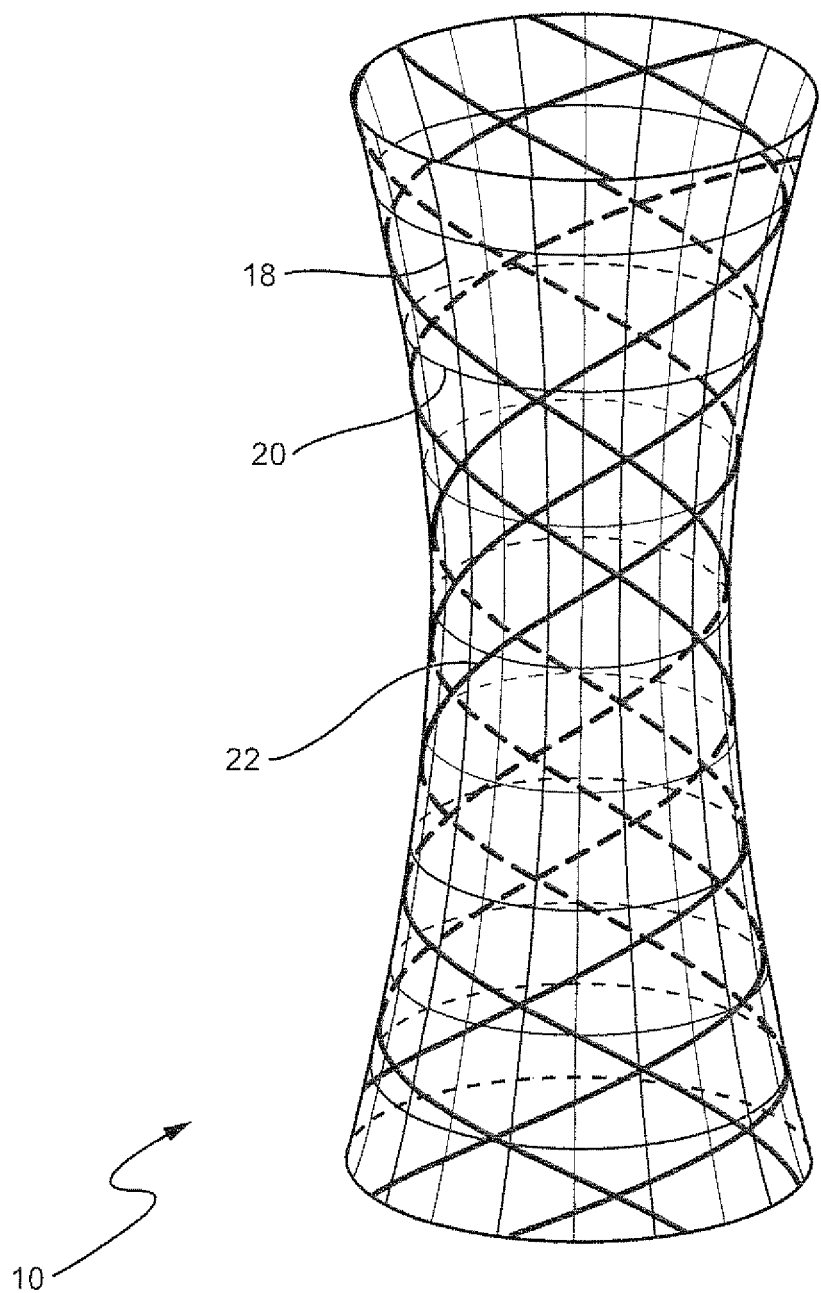
FIGS. 2A and 2B show details of a long bone matrix.
Figure 2B:
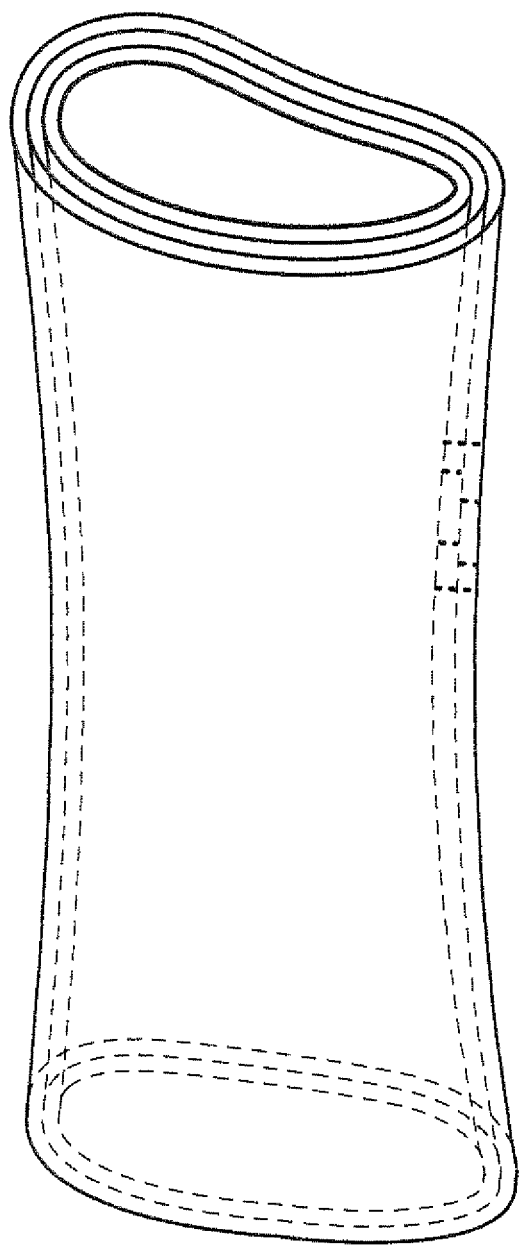

In one embodiment, with reference to FIG. 1, the fibers of the base material may be in the pattern of a network with fibers arranged in horizontal 12, vertical 14 and oblique 16 orientations, such that the base material is able to impart tensile, shear, bending and compressive strength to the final composite. In another embodiment, with reference to FIG. 2A, the polymer matrix framework 10 can be made in a concentric cylindrical arrangement with several cylinders, depending on the load to which the bone or implant will be subjected. The cylinders may be made in the shape of specific bone or implant, and the structure is thus suitable as an intramedullary rod, or artificial joint. The cylinders are composed of fibers in vertical 18, horizontal 20 and spiral 22 arrangements to meet the demands of various stresses to which the bone is subjected. In another embodiment, adjacent cylinders are interconnected by transverse fibers running across all the cylinders in the same planes or in staggered fashion or a mixture of both (FIG. 2B).

Figure 3B:
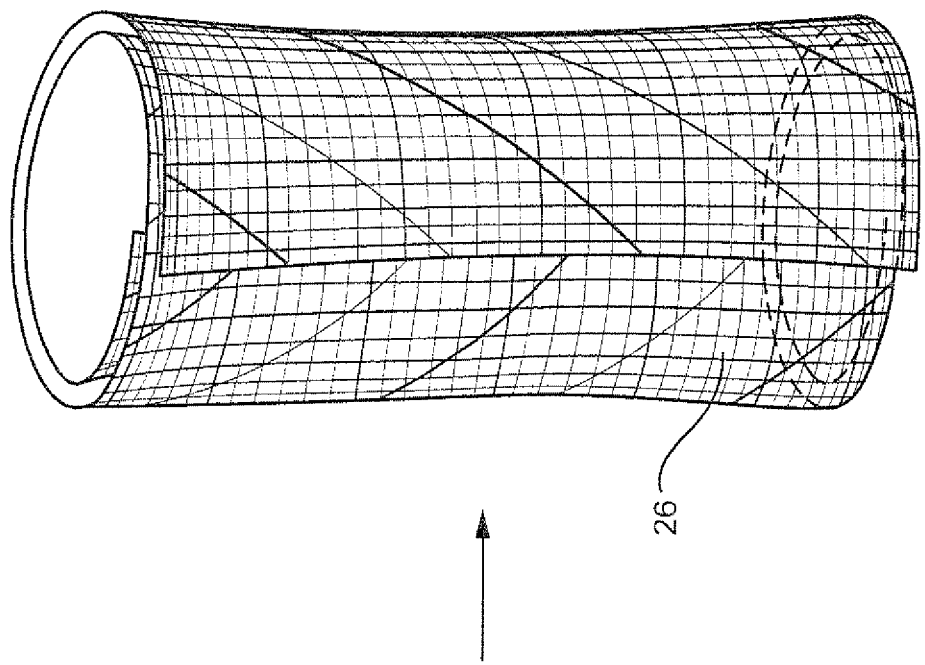
FIGS. 3A and 3B show an exemplary polymer matrix framework utilizing a spiral cylinder.
Figure 3A:
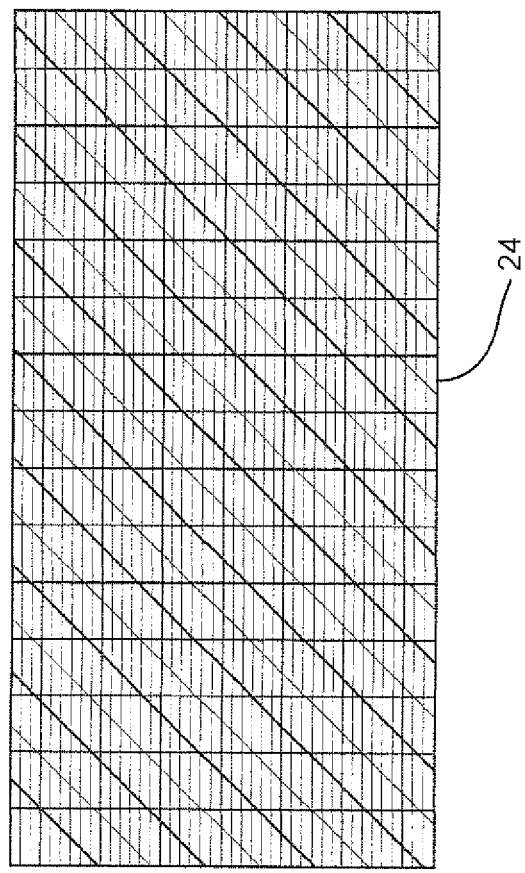

In still another embodiment, with reference to FIGS. 3A and 3B, the polymer matrix framework is made with a horizontal, vertical and spiral fiber network in the form of a sheet 24 which is then rolled into a multilayered cylinder 26. The center of a long bone is made relatively empty and may be used for insertion of a morphogenic factor such as hemopoietic factors to facilitate population of the construct with blood forming cells. The growth factor may be implanted as the inner layer of long bone to mimic the endosteum and on the outer wall to mimic the periosteum to induce recruitment of osteo-genic bone on both surfaces of the artificial device.

Figure 4:
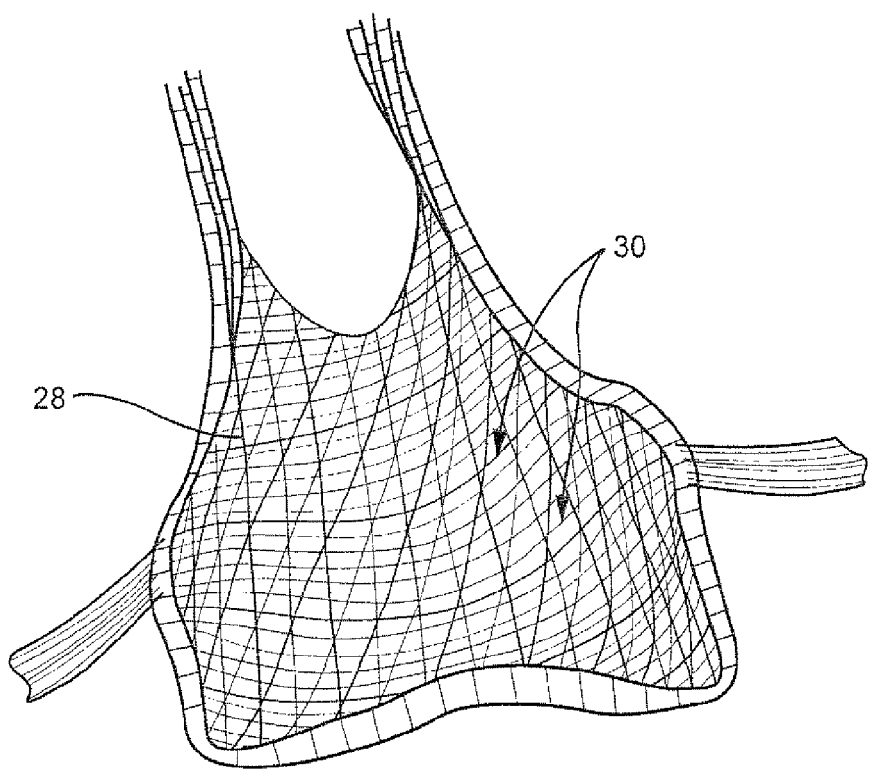
FIG. 4 shows an exemplary application to the end of a long bone.

The ends of the long bones, in another embodiment shown in FIG. 4, include cylindrical fibers 28 of lesser thickness than the cortical shaft bone, but a there is a dense network of fibers 30 throughout its width to resemble the metaphysic and the epiphysis of the long bone. This network will, in a later stage of processing, be impregnated with ceramic bone to impart physiologic resistance to compressive forces. For the attachment of tendons and ligaments, a stump of the polymer fibers, continuous with the matrix of the artificial bone, is developed at the anatomical sites of the artificial bone, for the insertions or origins of these structures.

Numerous mechanisms may be utilized to maintain the shape of the artificial bone or implant, such as the intramedullary rod. In one embodiment, while maintaining the shape of the construct on a mold, the fabric may be impregnated with a biocompatible, fast curing liquid substance which hardens and stiffens the construct as it dries, thereby allowing it to maintain the desired shape. Alternatively, the fabric itself may be manufactured at such a temperature that as it cools or warms up it hardens, thereby retaining the shape of the mold. Still further, the fabric may be maintained in the desired shape inside, outside or sandwiched within the wall of the mold, and impregnated with a stiffening substance.

The polymer matrix so constructed can then be impregnated with bone substitute such as ceramics. In one embodiment, the composite, with the polymer fabric in the shape of the bone or desired implant, may be formed by immersion into a mold containing ceramic in liquid form and allowed to set by altering the temperature. Alternatively, the polymer fabric may be placed in the mold and the ceramic poured into the mold and allowed to set incorporating the polymer matrix framework. The polymer matrix framework in the form of the desired structure may be sprayed with the ceramic bone substitute which then hardens to the stiffness of bone as it sets. The polymer matrix framework in the form of the desired device may alternatively be grit-blasted with the bone ceramic. Still further, the cylinders of the device may be individually impregnated with the ceramic, and the cylinders so formed may then be inserted into each other and bonded together via the ceramic layers. In a preferred embodiment, the polymer sheet is rolled into a cylinder to produce the desired device, and the device is then impregnated with the ceramic using any one of the methods described above. Once impregnated, the polymer fabric becomes an artificial bone composite.

In order for the remodeling of the artificial bone or implant to occur expeditiously, channels may be created in the artificial bone composite, and the channel walls may be coated with angiogenic factors to facilitate in-growth of vessels and bone forming cells. The vascular channels may be created in any suitable manner.

In one embodiment, the polymer fiber matrix in the shape of the desired bone or implant is made of a fine network of fibers with variable dimensions of spaces between the fibers depending on the function of the bone or device as described above with reference to FIG. 1. The device is then placed on a mold and hardened by immersion in, or spraying with a substance that hardens with cooling or heating. The structure is then sprayed with liquid ceramic bone substitute. The composite will have porosity of variable amounts depending on the function for which it is intended.

Figure 5:
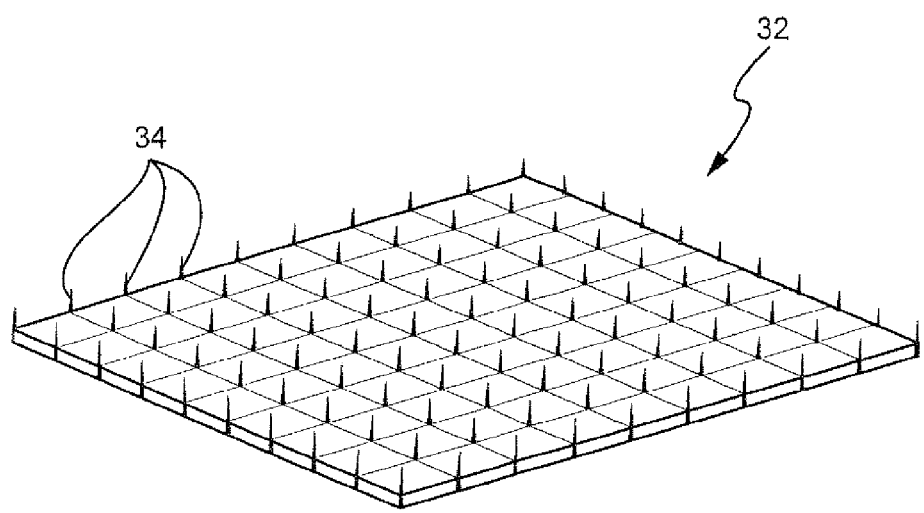
FIG. 5 shows a sheet used for generating porosity for vascular in-growth.

Alternatively, with reference to FIG. 5, at the time of manufacture, the polymer matrix framework may be wrapped with a porous sheet of absorbable material 32 which has spikes 34 of variable density on different areas of its surface. The sheet 32 is wrapped around the fiber framework such that the surface containing the spikes 34 is adjacent the fiber framework. The sheet 32 is wrapped such that the spikes 34 penetrate into the framework. The ceramic in liquid or molten form is then applied to the framework using any of the above embodiments. The sheet material may be removed by various techniques once the composite has hardened. Removal of the spikes 34 and the sheet 32 may include dissolution in appropriate chemical, heating, or in vivo dissolution in body fluid.

In yet another alternative, the mold in which the device is produced may be armed with spikes which run horizontally and in other planes. The mold may be in multiple parts that are assembled together around the polymer matrix framework with the spikes penetrating into the framework. The ceramic bone is then used to produce the bone composite in one of the embodiments described earlier. The spikes, which may be retractable from the composite by some mechanism, are then removed at an appropriate time in the curing process.

The composite device may still alternatively be produced without porosity, but at an appropriate stage in the curing process, the device may be micro-drilled to produce the appropriate amount of porosity to permit vascular in-growth in the various parts of the artificial device.

The artificial bone constructed with the structure and methods described will preferably have the following characteristics:

Trabecular network of ceramic plates augmented with polymer network to confer compressive strength to the artificial bone ends while minimizing the weight of the bone.

The porosity conferred by micro-drilling of the fabricated composite will allow neo-vascularization and population of the bone with host marrow cells.

The concentric cylindrical arrangement of the polymer fibers produced by wrapping the sheet of polymer matrix framework will mimic the bone lamellae and impart the bending, shear and torsional strength to the long bone shafts.

Application of bone morphogenic protein and hemopoietic factors will encourage recruitment of host cells to form new bone and allow blood formation within the artificial bone.

For the attachment of the tendons and ligaments, a stump of the polymer fabric in continuity with the bone matrix is developed at anatomical sites of the artificial bone, similar to the natural bone, to facilitate surgical attachment.

The composite may be used to act as a carrier for various substances to induce osteosynthesis (BMPs), hemopoietic factors to stimulate blood formation in the artificial bone, and/or antibiotics of slow controlled release both to prevent infection or treatment of existing osteomyelitis.

Examples of the devices that may be developed from the composite are illustrated in FIGS. 6A-11.

Figure 6A:
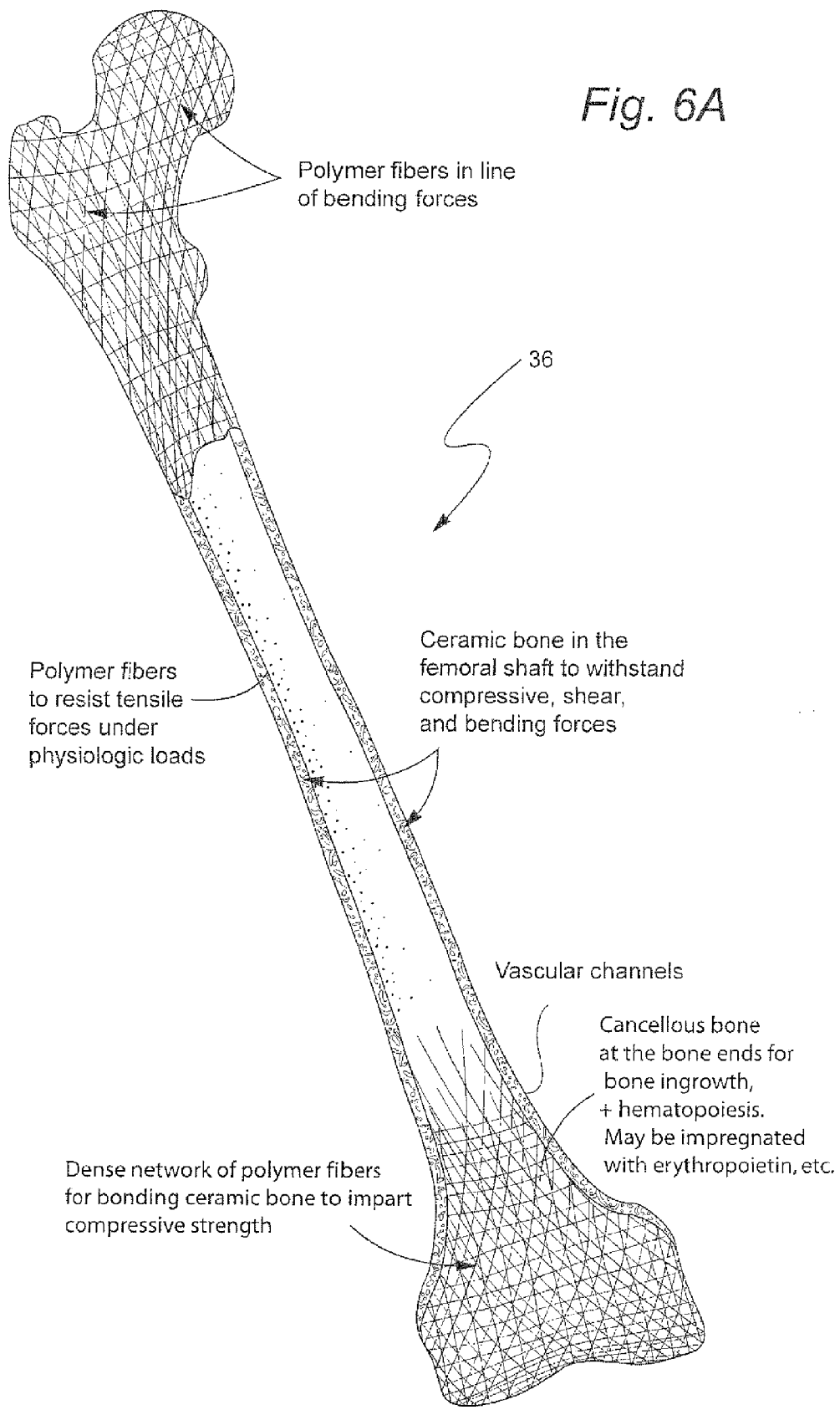
FIG. 6A shows a coronal section of an artificial femur.
Figure 6B:
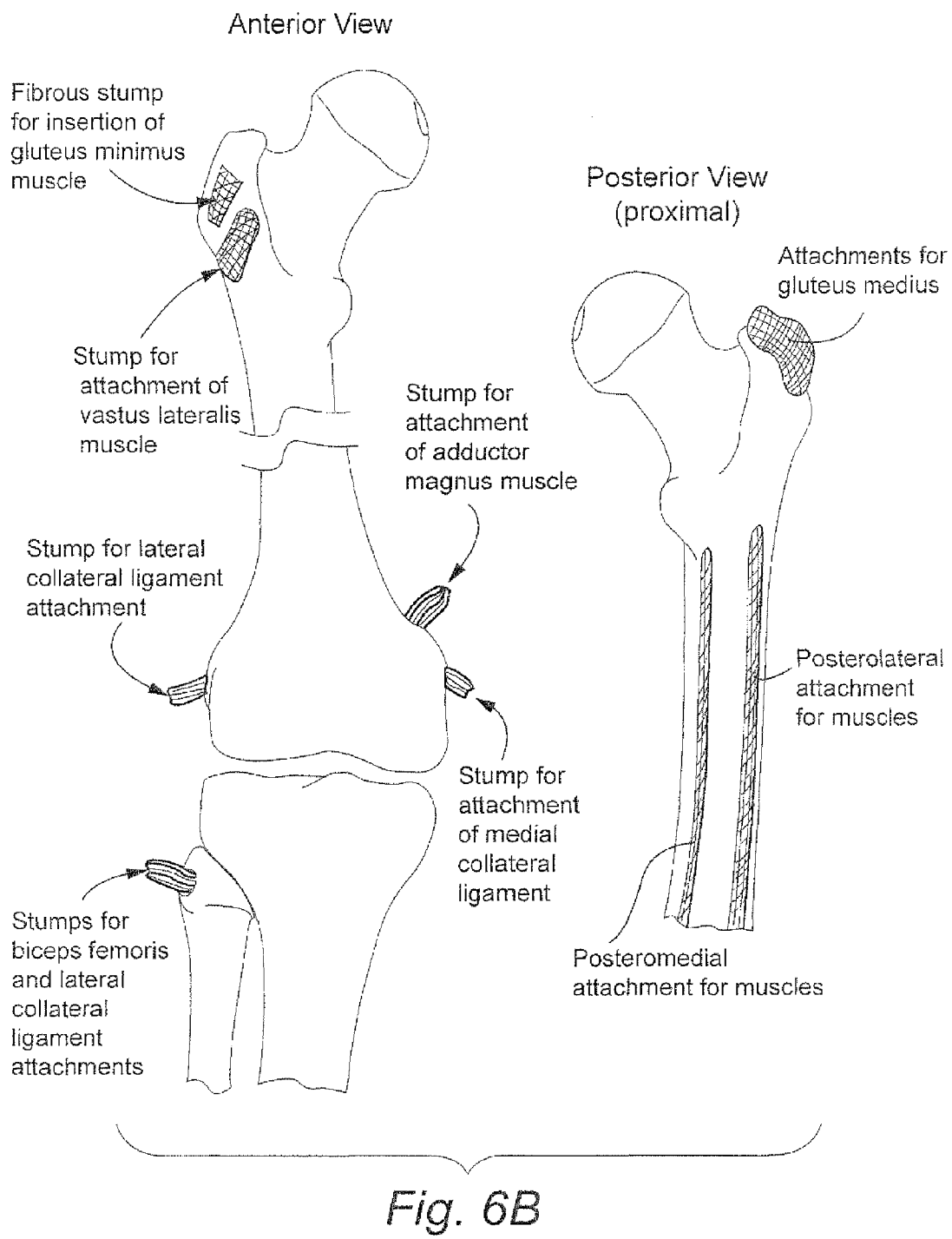
FIG. 6B shows femoral attachments for muscles and ligaments.
Figure 6C:
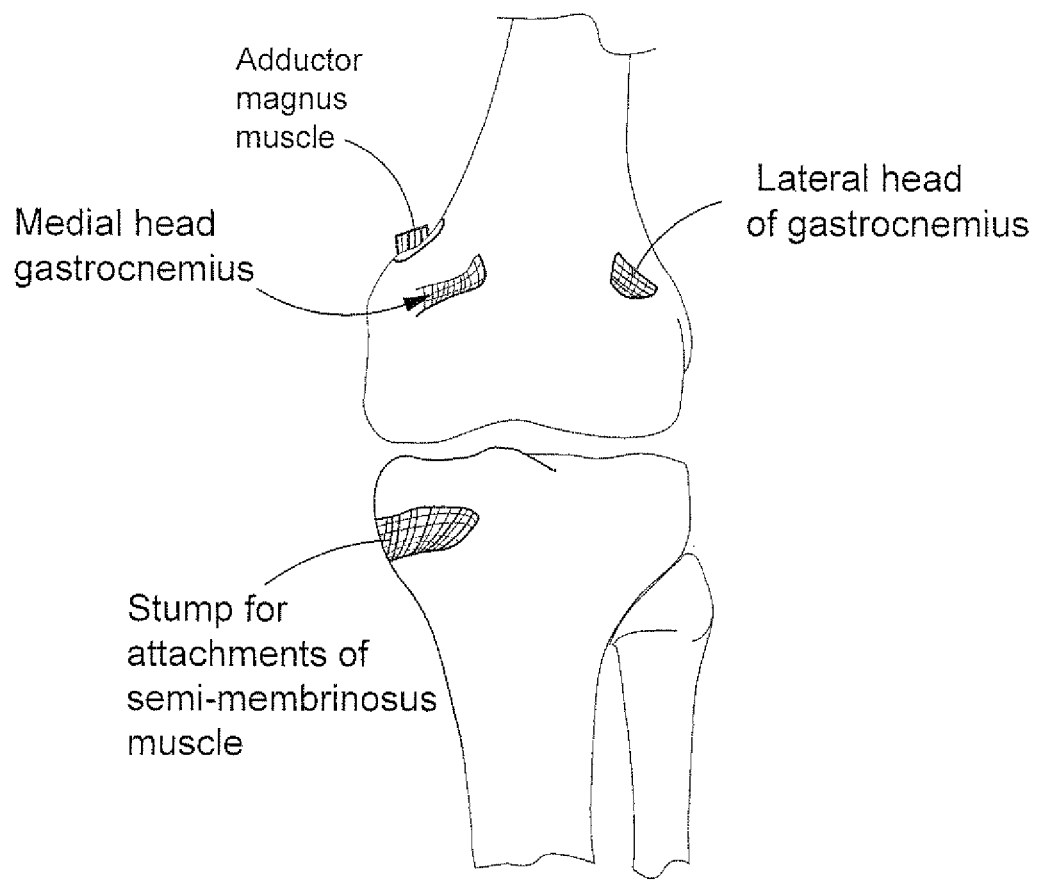
FIG. 6C is a distal femur posterior view.

Long bones may be developed such as the femur, humerus, radius, ulna, metacarpal bones etc. FIG. 6A is an example of a femur 36. The shaft and the bone ends are designed according to any of the embodiments described above. The density, thickness and orientation of the polymer fibers are varied from region to region in the bone to meet different physiological and biomechanical requirements. The fibers are tightly packed, and the cortex is thick in the shaft where the tensile, bending, shear and torsional forces tend to be higher. The bone ends are expanded and have cancellous-bone-like matrix to withstand compressive forces and also act as a site for blood cell formation. FIGS. 6B and 6C show the sites for the attachment of various tendons and ligaments, where stumps of the polymer are developed to facilitate surgical attachments.

Figure 7A:
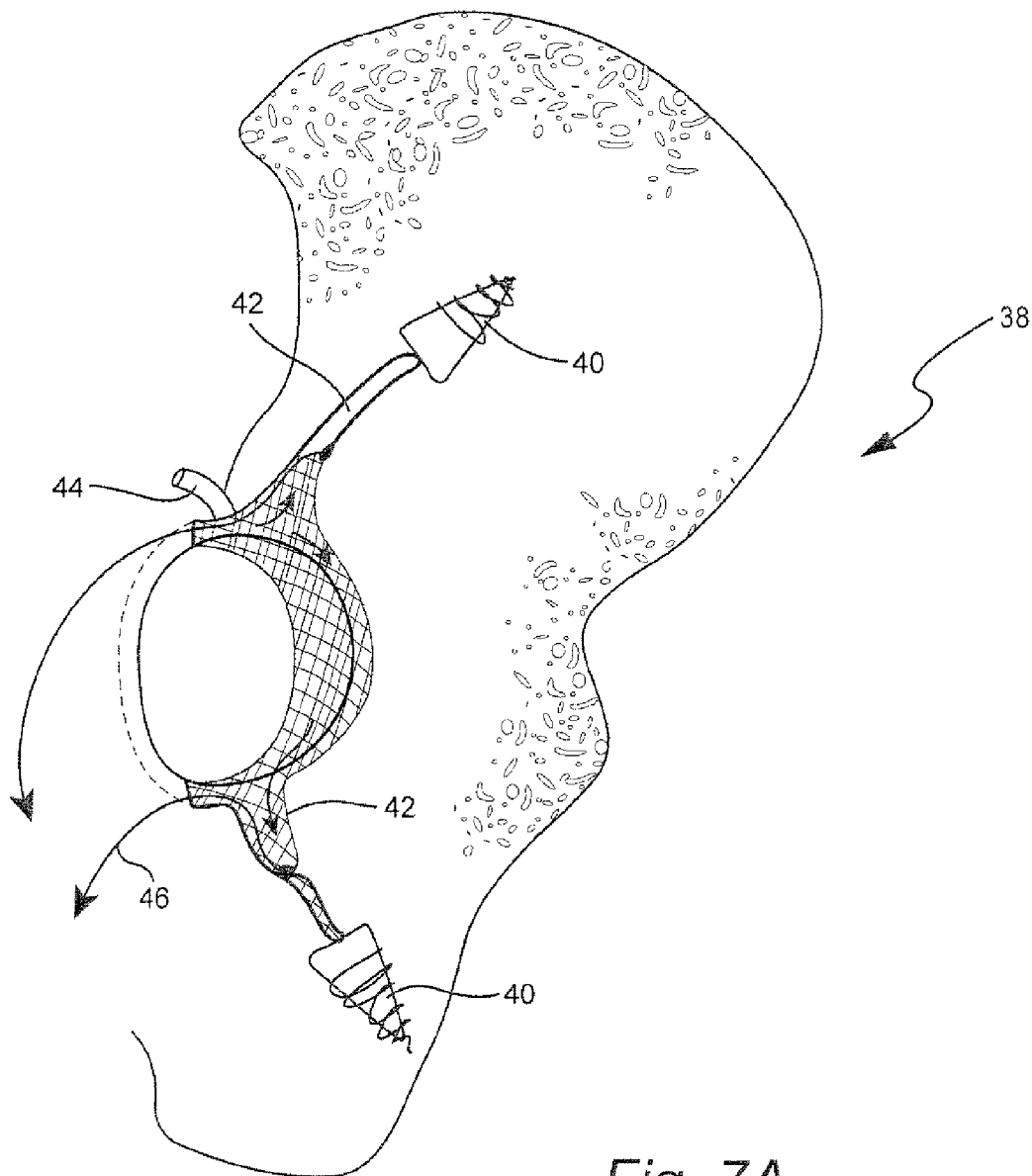
FIG. 7A shows an exemplary acetabulum.

FIG. 7A illustrates an embodiment of an artificial acetabular cup 38. The artificial cup 38 is developed in the manner described above to make a composite of polymer fiber matrix and ceramic bone furnished with appropriate porosity and impregnated with various factors such as the bone morphogenic protein. Further, on its bone surface, polymer fiber pegs 40 are attached at sites which correspond to the ischium, the pubic ramus and the iliac wing. The pegs are connected to the rim of the acetabular cup via channels 42 through which the ceramic bone or another type of bone grout may be injected into the peg via a nozzle 44 to enhance fixation. In a preferred embodiment, bone anchors (also made from biologic material) are inserted into the ischial tuberosity, the pubic ramus and the ilium. A strong fiber suture material 46 is attached to the fiber matrix peg and is used to pull the peg into the hole keyed into the ischial tuberosity, the pubic ramus and the iliac wing. These pegs are then injected with bone grout to enhance fixation once the acetabular cup has been well fixed into the prepared host acetabular bed. The articular surface of the artificial cup may be made of ceramic reinforced with polymer fibers.

Figure 7B:
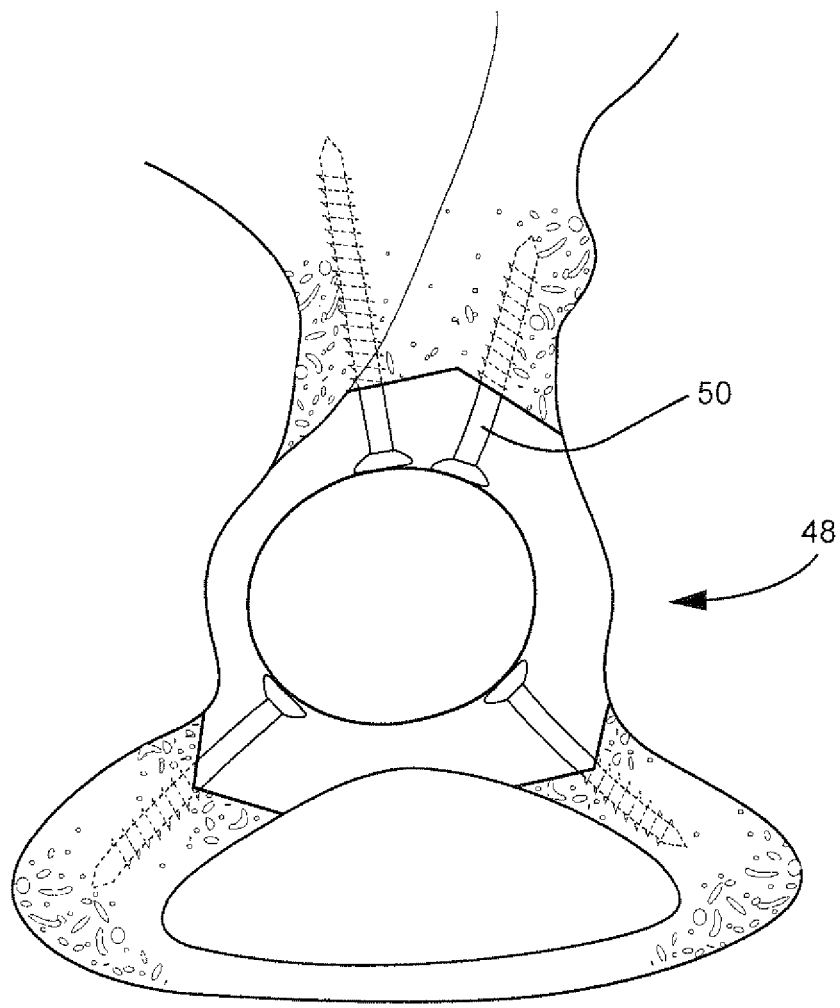
FIG. 7B shows a replacement of an acetabular defect.

In the case of acetabular defects, with reference to FIG. 7b, either the entire acetabulum or parts thereof may be replaced by artificial acetabulum complete with its walls and the ischial, iliac and pubic processes for fixation to the host skeleton. The fixation may be enhanced by insertion of cannulated and fenestrated biologic screws 50 through which bone grout may be injected to facilitate immediate stable fixation. Bone defects at the joints or in the shaft of the long bones may be similarly replaced and fixed in the various ways described above.

Figure 8:
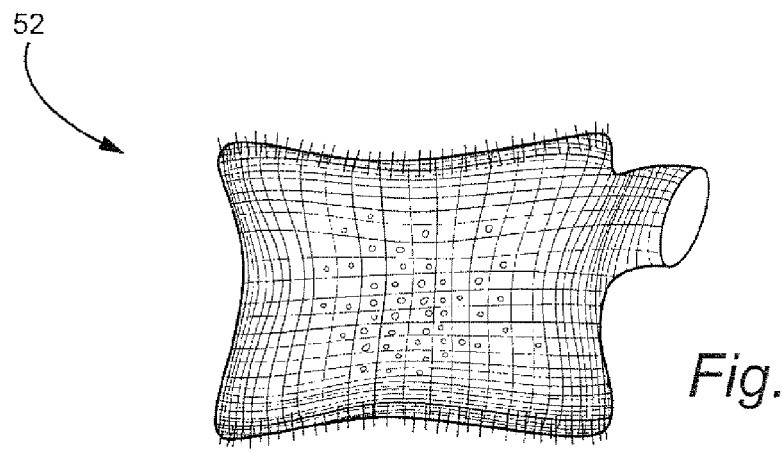
FIG. 8 illustrates an artificial vertebral body.

FIG. 8 shows an exemplary vertebral body 52. The polymer fiber matrix framework is constructed in such a way that appropriate densities of the fibers are used in different areas of the vertebra to meet the physiologic and biomechanical requirements. The endplates need significant reinforcement with the components of the composite to withstand compressive forces. The porosity of the vertebrae will enhance vascular in-growth, and impregnation with various factors will enhance host cell population in the artificial bone.

Figure 9:
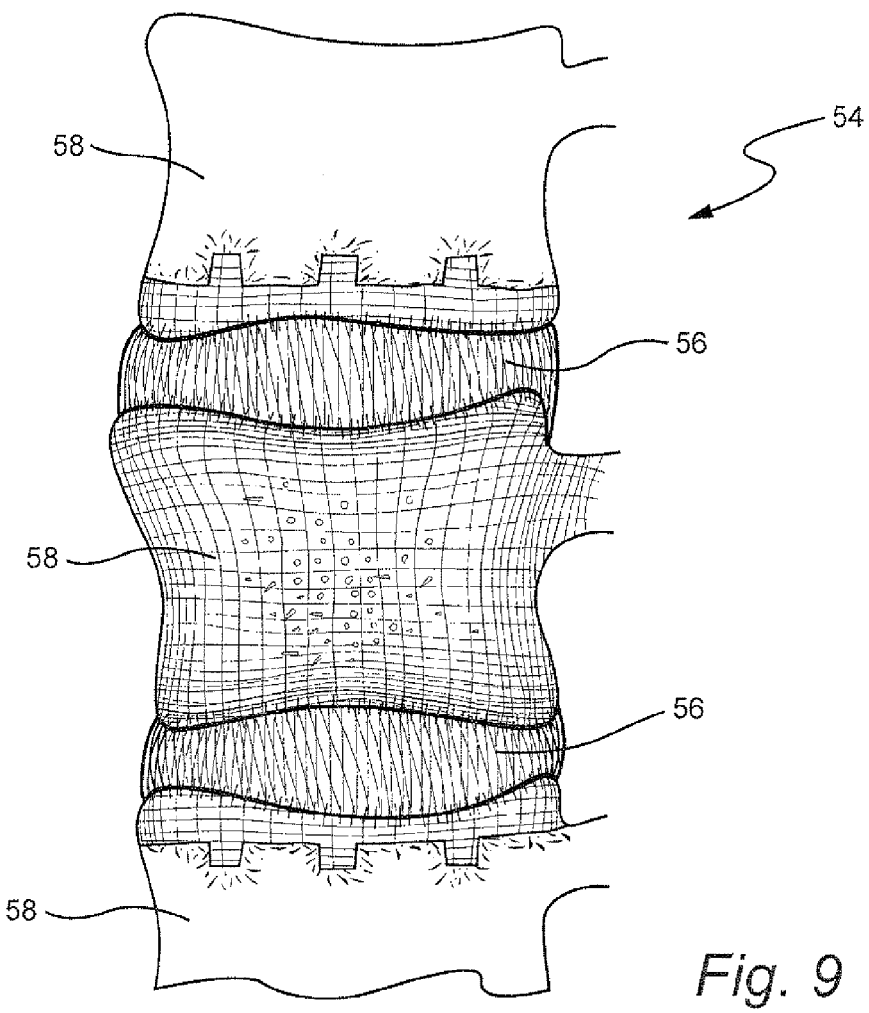
FIG. 9 shows an artificial motion segment.
Figure 10:
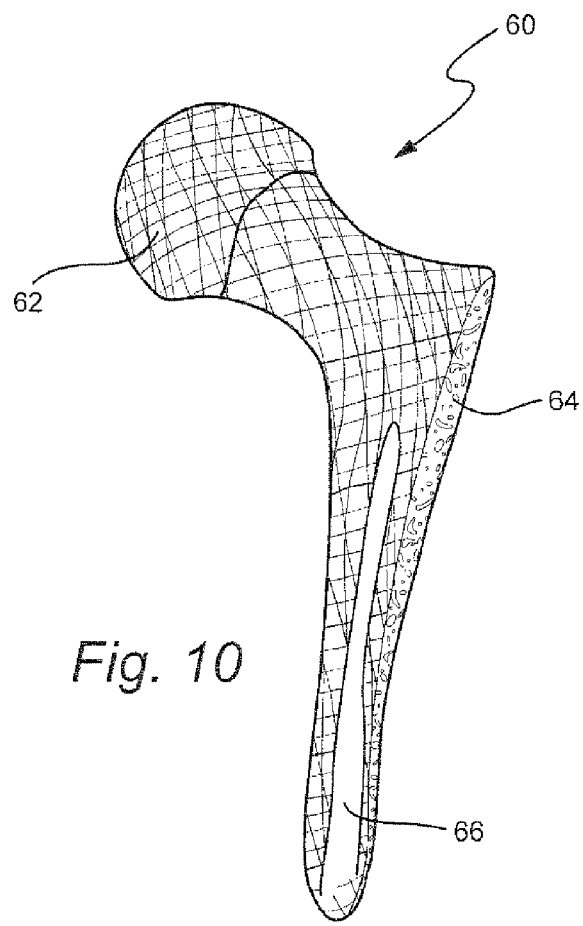
FIG. 10 illustrates an artificial proximal femur for arthroplasty.

FIG. 9 shows an exemplary spinal motion segment unit 54. The use of this application is most likely in the treatment of vertebral fractures in a young person; pathological fractures in cases of a localized tumor of multilevel disc disease not responding to non-operative measures and the like. The motion segment unit includes an intervertebral disc 56 and adjacent vertebral segments 58. This embodiment is preferred because it allows the polymer matrix of the vertebral body to be continuous with the disc annulus fibers, which permits excellent bone fixation. The superior and inferior artificial vertebral endplates may be attached to the host bone via pegs, biologic screws, bone anchors and bone grouts singly or in various combinations. The artificial vertebral body may be fixed to the host's posterior vertebral elements through the artificial bone pedicle processes. This fixation may be accomplished by biologic bone screw and bone grout through fenestrations in the screw shaft.

Acetabular replacement with artificial bone components has been described above. A similar device may be used for the replacement of the glenoid in the shoulder, and the proximal ulna and other ball and socket joints. The articular ends of long bones may also be replaced with artificial bone. In one embodiment, with reference to FIG. 10, the proximal femur 60 may be replaced with an artificial component including a femoral head 62 developed as described above (and with hardened and fiber-reinforced articular surface for durability), a femoral neck 64, and a shaft component 66. The shaft 66 may be tubular or solid and may be fixed to the host femur with bone grout or by press-fit. The proximal and distal humerus and other long and cubical bones may be similarly replaced.

Figure 11:
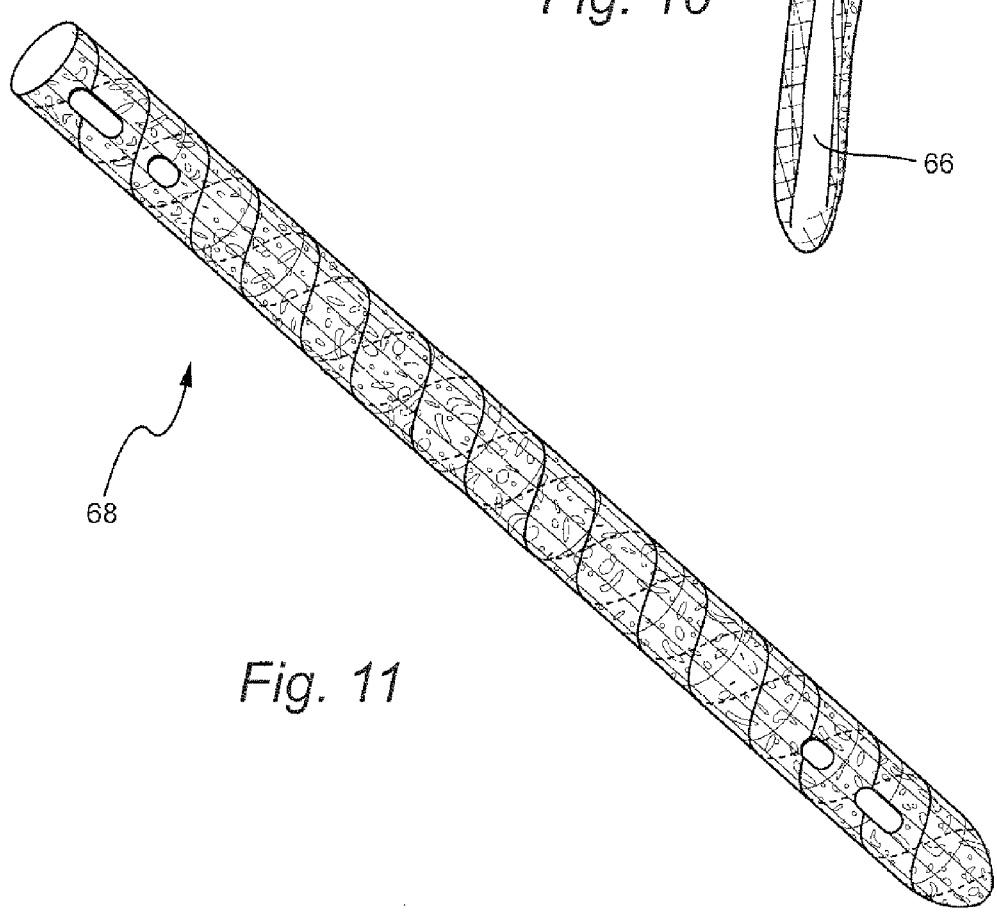
FIG. 11 shows composite artificial fracture fixation implants.

Intra-medullary rods are commonly used for fractures of long bones. With reference to FIG. 11, a tubular or solid bone composite 68, produced in according to one of the methods described above, may be used for an intra-medullary rod 68. The polymer fiber matrix density and orientations are important to impart resistance to various stresses. The rod 68 may or may not have holes for transfixation to the proximal and distal fracture fragments to prevent shortening of the bone during the healing process. Further, the rods may be furnished with fenestrations at the fracture site for injection of biologic bone grout to enhance immediate fixation and stabilization. The artificial bone rod 68 may be coated with various growth factors, including the bone morphogenic protein to facilitate population of the implant by the host bone cells. The implant may be furnished with porosity to facilitate vascular in-growth.

The composite artificial bone produced as described above may also be used to produce bone plates and screws. Instead of composite cylinders, slabs of the artificial bones may be produced. Appropriate thickness and stiffness of the slabs may be used from which individual plates may be produced. In another embodiment, the polymer fiber matrix for specific type and size of bone plate may be produced and the composite developed in one of the embodiments described earlier. The plates may be static, compression or locking plates to address the different fracture situation. The plates may be site specific such as the distal femoral locking plate, proximal or distal humeral or hand fracture plate.

With the structure and methods of the described embodiments, an artificial composite structure is achieved that is similar to natural bone with comparable properties.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A biologic artificial bone comprising:
an artificial fiber material formed from a synthetic polymer with mechanical properties similar to type I collagen, wherein the artificial fiber material is formed into a cast shaped corresponding to a human bone or a bone implant, and wherein the artificial fiber material comprises fibers formed in a fiber network with fibers arranged in multiple orientations in a single sheet, wherein the artificial fiber material comprises fibers formed in a fiber network with fibers arranged in horizontal, vertical and oblique orientations;
a biocompatible liquid substance impregnated in the fiber material, the biocompatible liquid substance hardening and stiffening the fiber material;
a bone substitute impregnated in the hardened and stiffened fiber material forming an artificial bone composite, wherein the artificial bone composite has structural characteristics by virtue of the artificial fiber cast, biocompatible liquid substance and the bone substitute such that the artificial bone composite retains its shape after installation; and
vascular channels formed in the artificial bone composite prior to installation to facilitate in-growth of vessels and bone forming cells.

2. A biologic artificial bone according to claim 1, wherein the bone substitute comprises ceramics.

3. A biologic artificial bone according to claim 1, wherein the channels are coated with angiogenic factors.

4. A biologic artificial bone according to claim 1, wherein the artificial bone composite is wrapped with a porous sheet of absorbable material having dissolvable spikes of variable density on one side thereof, the porous sheet being wrapped on the artificial bone composite with the spikes facing inward to penetrate the artificial bone composite, thereby creating the vascular channels for vascular in-growth after implantation of the biologic artificial bone.

5. A biologic artificial bone according to claim 1, further comprising a single or multiple stumps of the artificial fiber material in continuity with the artificial bone composite for attachment of tendons after implantation of the biologic artificial bone.

6. A biologic artificial bone according to claim 1, further comprising a trabecular network of ceramic plates augmented with a polymer network that confer compressive strength to ends of the artificial bone.

7. A biologic artificial bone comprising:
an artificial fiber material formed from a synthetic polymer with mechanical properties similar to type I collagen, wherein the artificial fiber material is formed into a cast shaped corresponding to a human bone or a bone implant, and wherein the artificial fiber material comprises fibers formed in a fiber network with fibers arranged in multiple orientations in a single sheet, wherein the artificial fiber material comprises fibers formed in a fiber network with fibers arranged in vertical, horizontal and spiral orientations defining a concentric cylindrical arrangement of fibers;
a biocompatible liquid substance impregnated in the fiber material, the biocompatible liquid substance hardening and stiffening the fiber material;
a bone substitute impregnated in the hardened and stiffened fiber material forming an artificial bone composite, wherein the artificial bone composite has structural characteristics by virtue of the artificial fiber cast, biocompatible liquid substance and the bone substitute such that the artificial bone composite retains its shape after installation; and
vascular channels formed in the artificial bone composite prior to installation to facilitate in-growth of vessels and bone forming cells.

8. A biologic artificial bone according to claim 7, wherein the bone substitute comprises ceramics.

9. A biologic artificial bone according to claim 7, wherein the channels are coated with angiogenic factors.

10. A biologic artificial bone according to claim 7, wherein the artificial bone composite is wrapped with a porous sheet of absorbable material having dissolvable spikes of variable density on one side thereof, the porous sheet being wrapped on the artificial bone composite with the spikes facing inward to penetrate the artificial bone composite, thereby creating the vascular channels for vascular in-growth after implantation of the biologic artificial bone.

11. A biologic artificial bone according to claim 7, further comprising a single or multiple stumps of the artificial fiber material in continuity with the artificial bone composite for attachment of tendons after implantation of the biologic artificial bone.

12. A biologic artificial bone according to claim 7, further comprising a trabecular network of ceramic plates augmented with a polymer network that confer compressive strength to ends of the artificial bone.

13. A biologic artificial bone comprising:
- an artificial fiber material formed from a synthetic polymer with mechanical properties similar to type I collagen, wherein the artificial fiber material is formed into a cast shaped corresponding to a human bone or a bone implant, and wherein the artificial fiber material comprises fibers formed in a fiber network with fibers arranged in multiple orientations in a single sheet, wherein the artificial fiber material comprises fibers formed in a fiber network with fibers arranged in vertical, horizontal and spiral orientations defining a fibrous sheet rolled into a multilayer cylinder;
- a biocompatible liquid substance impregnated in the fiber material, the biocompatible liquid substance hardening and stiffening the fiber material;
- a bone substitute impregnated in the hardened and stiffened fiber material forming an artificial bone composite, wherein the artificial bone composite has structural characteristics by virtue of the artificial fiber cast, biocompatible liquid substance and the bone substitute such that the artificial bone composite retains its shape after installation; and
- vascular channels formed in the artificial bone composite prior to installation to facilitate in-growth of vessels and bone forming cells.

14. A biologic artificial bone according to claim 13, wherein the bone substitute comprises ceramics.

15. A biologic artificial bone according to claim 13, wherein the channels are coated with angiogenic factors.

16. A biologic artificial bone according to claim 13, wherein the artificial bone composite is wrapped with a porous sheet of absorbable material having dissolvable spikes of variable density on one side thereof, the porous sheet being wrapped on the artificial bone composite with the spikes facing inward to penetrate the artificial bone composite, thereby creating the vascular channels for vascular in-growth after implantation of the biologic artificial bone.

17. A biologic artificial bone according to claim 13, further comprising a single or multiple stumps of the artificial fiber material in continuity with the artificial bone composite for attachment of tendons after implantation of the biologic artificial bone.

18. A biologic artificial bone according to claim 13, further comprising a trabecular network of ceramic plates augmented with a polymer network that confer compressive strength to ends of the artificial bone.

* * * * *